US 7,361,208 B2

(12) United States Patent
Botelho et al.

(10) Patent No.: US 7,361,208 B2
(45) Date of Patent: Apr. 22, 2008

(54) CHROMATOGRAPHY OVEN WITH HEAT EXCHANGE AND METHOD OF USE

(75) Inventors: Jim Botelho, Danbury, CT (US); Stephen Pignataro, Jr., Norwalk, CT (US); John Mezzoni, Milford, CT (US); John H. Vanderhoef, Stratford, CT (US)

(73) Assignee: PerkinElmer LAS, Inc., Boston, MA (US)

( * ) Notice: Subject to any disclaimer, the term of this patent is extended or adjusted under 35 U.S.C. 154(b) by 152 days.

(21) Appl. No.: 11/122,148

(22) Filed: May 4, 2005

(65) Prior Publication Data
US 2005/0258088 A1    Nov. 24, 2005

Related U.S. Application Data

(60) Provisional application No. 60/521,479, filed on May 4, 2004.

(51) Int. Cl.
*B01D 53/02* (2006.01)
*G01N 30/02* (2006.01)

(52) U.S. Cl. .............................. 95/87; 96/101; 96/106; 73/23.25; 73/23.35

(58) Field of Classification Search ................. 96/101, 96/102, 103, 107; 95/82, 87; 73/23.25, 73/23.35, 23.36, 23.39, 23.4; 422/89; 210/198.2, 210/656
See application file for complete search history.

(56) References Cited

U.S. PATENT DOCUMENTS

| | | | | |
|---|---|---|---|---|
| 3,165,147 A | * | 1/1965 | Roof et al. ................. | 165/256 |
| 3,385,099 A | * | 5/1968 | Jentzsch et al. ............ | 73/23.25 |
| 3,422,603 A | * | 1/1969 | Redmond, Jr. ............... | 96/103 |
| 4,050,911 A | * | 9/1977 | Welsh .......................... | 96/103 |
| 4,181,613 A | * | 1/1980 | Welsh et al. ................. | 210/179 |
| 4,286,456 A | * | 9/1981 | Sisti et al. .................. | 73/23.25 |
| 4,580,036 A | * | 4/1986 | Hunt et al. .................. | 219/400 |
| 4,599,169 A | * | 7/1986 | Ray ........................... | 210/175 |
| 4,771,628 A | * | 9/1988 | Sisti et al. .................. | 73/23.25 |
| 5,634,961 A | | 6/1997 | Gordon ......................... | 95/17 |

(Continued)

OTHER PUBLICATIONS

*Principles of Methods for Separation*; Mar. 22, 2005 (www.agsci.ubc.ca/fnh/courses.html).

(Continued)

*Primary Examiner*—Duane Smith
*Assistant Examiner*—Robert A Clemente
(74) *Attorney, Agent, or Firm*—St. Onge Steward Johnston & Reens LLC (57) ABSTRACT

Methods and systems for cooling gas chromatography ovens that comprise a housing having a fluid entry and a sleeve positioned within the housing to provide a fluid gap between the inner surface of the housing and the outer surface of the sleeve, where the sleeve is coupled to the fluid entry, and where a cooling fluid from the fluid entry traverses the inner layer of the sleeve and thereafter the outer layer of the sleeve via the fluid gap. In one embodiment, the housing includes at least one adjustable fluid exit, and the fluid gap is in fluid communications with the fluid exit(s). The fluid entry and the sleeve can be concentric, and the sleeve can include a heating element. A fan can be positioned to drive the cooling fluid from the fluid entry.

46 Claims, 7 Drawing Sheets

U.S. PATENT DOCUMENTS

| | | | |
|---|---|---|---|
| 5,744,029 A | | 4/1998 | Li et al. .................... 210/198 |
| 5,807,426 A | * | 9/1998 | Ohtsuki et al. ............... 96/102 |
| 5,830,262 A | * | 11/1998 | Marchini et al. ............. 96/105 |
| 5,837,883 A | * | 11/1998 | Itoi ........................... 73/23.37 |
| 6,103,112 A | * | 8/2000 | Sutton et al. ............ 210/198.2 |
| 6,248,158 B1 | * | 6/2001 | Abdel-Rahman et al. ..... 96/101 |

OTHER PUBLICATIONS

*Thermal Ceramics—Blanket Products*, Mar. 2005.
*Thermal Ceramics—BTU-Block Board 1807/18*, Mar. 2005.
*CU Boulder Organic Chemistry Undergraduate Courses—Lab Techniques*, Mar. 22, 2005 (www.orgchem.colorado.edu.html).

* cited by examiner

CHROMATOGRAPHY OVEN WITH HEAT EXCHANGE AND METHOD OF USE

RELATED APPLICATIONS

This application claims priority to U.S. Provisional Application No. 60/521,479 filed May 4, 2004 herein incorporated by reference.

FIELD

This invention relates generally to gas chromatography, and more specifically to an improvement in a gas chromatography oven to achieve improved heat exchange.

BACKGROUND

Gas chromatography is performed in a special instrument where a small amount of liquid mixture is injected into an apparatus where it is volatized in a heated chamber. The volatized mixture is swept through a column in a stream of gas, such as helium or neon under conditions where its components separate into pure compounds. The column is located in a heated oven in order to facilitate the separation. Just before each compound exits the instrument, it passes through a detector, which sends an electronic message to the recorder, which responds by printing a peak on a piece of paper identifying the compound.

Typically the column is heated by placing the column in an oven. The heat facilitates compound separation by raising the column temperature and speeding up the compounds in the mixture. For precise work, column temperature may be controlled to within tenths of a degree. The optimum column temperature is dependent upon the boiling point of the sample. Generally, a temperature slightly above the average boiling point of the sample results in an elution time of 2-30 minutes. If a sample has a wide boiling range, then temperature programming can be useful. The column temperature is increased (either continuously or in steps) as separation proceeds.

Accordingly, analytes of interest are assayed at different temperatures, including high temperatures such as 500° C., and it is necessary to cool the oven and the column prior to testing additional samples. Long cooldown periods are problematic because they lengthen the sample cycle time reducing instrument productivity. Delay is compounded in high throughput analysis where a gas chromatograph is needed to analyze a large number of samples containing the same or different analytes of interest. Users waste time waiting for the column and oven to cool prior to running additional samples.

Ventilation systems including fans have been added to the gas chromatograph to blow air into the oven and onto the column between runs. However, conventional designs are slow to cool for there are considerable flow restrictions which impede the air flow throughout the oven. Furthermore, certain designs allow the cooling inlet air to mix with exhausting air resulting in a slower, less efficient cool down of the oven. Moreover, temperature gradients may form in the oven reducing the consistency or uniformity of the cooling down components.

Prior art of interest includes one system which relates to a chromatography oven which includes a fan within a housing adjacent to rear walls, an ambient air intake vent in the rear wall, and an exhaust vent within a rear corner of one of the side walls adjacent to the rear wall for exhausting the tangential flow of air created by the rotating fan. However, this design has considerable flow restrictions which impede the air flow throughout the oven resulting in a less efficient cool down.

Of further interest is another prior art system which relates to an apparatus having a first compartment including a chromatography oven with fan for circulating heated air over the columns while the oven is closed and for drawing in ambient temperature cooling air in the first compartment into the oven while the oven is open. Ambient air is drawn into a tortuous path in the first compartment. Cooling air from the second compartment flows into the first compartment via openings in the baffle. The cooling air flows over the oven exterior and is at least partially drawn into the oven by an oven fan while the oven is open. The oven heater, coaxial with the blades, is located between an oven wall and blades. A ring baffle, having approximately the same diameter as and coaxial with the blades, is located between the wall and the blades. A fan outside of the oven draws air from the oven through an outlet while the oven is open. The second fan is separated from an inlet for the oven by a baffle having an opening through which air is drawn by the second fan while the oven is closed. The second compartment includes a casing for fluid flow controllers for the columns, which casing is maintained at constant temperature by ambient air drawn around the second compartment. However this design impedes air flow because the air entering the oven counters air flow leaving the oven reducing the efficiency of the cooling. Furthermore, the baffle impedes airflow and produces a temperature gradient in the oven which results in a less efficient cool down. Moreover, this device requires two fans to circulate airflow which takes up additional energy and is noisy.

Of further interest is another prior art system relating to gas chromatography (GC) system employing a low-thermal-mass oven in which intake and exhaust vent apertures are aligned with respect to the rotational axis of the stirring fan. The poppets of the vent dynamically vent to ambient the air-flow generated by the stirring fan. The geometry of the vents cooperates with the axial and radial components of the stirring fan to promote conical vortex air flow, to facilitate mass-flow interchange with ambient air. However, the ventilation system includes a bulky vent servo in order to drive a carriage assembly which opens a front exhaust poppet. Exhaust leaves the front of the oven never circulating back over the oven skin resulting in reduced efficiency.

SUMMARY

It is an object of the present invention to provide an oven that reduces or eliminates air flow restrictions which impede air flow within a gas chromatography oven.

Another object of the present invention is to provide a gas chromatography oven that reduces mixing of inlet air and exhausting air.

Another object of the present invention is to provide a gas chromatography system which is highly efficient.

Another object of the present invention is to provide a gas chromatography oven that controls heat exchange between the airflow and the gas chromatography oven components.

The present teachings include gas chromatography ovens that comprise a housing having a fluid entry and a sleeve positioned within the housing to provide a fluid gap between the inner surface of the housing and the outer surface of the sleeve, where the sleeve is coupled to the fluid entry, and where fluid from the fluid entry traverses the inner layer of the sleeve and thereafter the outer layer of the sleeve via the fluid gap. In one embodiment, the housing includes at least one fluid exit, and the fluid gap is in fluid communications with the fluid exit(s). The fluid entry and the sleeve can be concentric, and the sleeve can include a heating element. In an embodiment, also included is a fan positioned to drive at least one fluid from the fluid entry into the sleeve.

The gas chromatography oven housing can include a wall, at least a portion of which is adjustable to prevent fluid from entering the fluid entry. Further, the oven housing can include at least one fluid exit, and, a wall at least a portion of which is adjustable to prevent fluid from exiting the fluid exit(s).

The present teaching also include methods of cooling a gas chromatography oven, where the method comprises providing a housing having a fluid entry, positioning a sleeve within the housing to provide a fluid gap between the inner surface of the housing and the outer surface of the sleeve, where the sleeve is coupled to the fluid entry, and where fluid from the fluid entry traverses the inner layer of the sleeve and thereafter the outer layer of the sleeve via the fluid gap, and, providing a cooling fluid to the fluid entry. Positioning can include concentrically positioning the sleeve and the fluid entry. The methods can also include controlling a fan positioned at the fluid entry to drive the cooling fluid from the fluid entry. In some embodiments, the methods include adjusting at least a portion of at least one wall of the housing to facilitate entry of the cooling fluid to the fluid entry, and/or adjusting at least a portion of at least one wall of the housing to facilitate exit of the cooling fluid from at least one fluid exit, where the at least one fluid exit is in fluid communications with the fluid gap.

The objectives of the present invention are met by providing a gas chromatography oven comprising: a housing having two end walls and a peripheral wall, a sleeve disposed within the housing, the sleeve having a peripheral wall spaced apart from the peripheral wall of the housing; and a fluid path defined by an interior of said sleeve, a first gap between at least one end wall and the sleeve, and a second gap between the peripheral wall of the sleeve and the peripheral wall of the housing, wherein air is forced through the sleeve, through the first gap between at least one end wall and the sleeve, and through the second gap between the peripheral wall of the sleeve and the peripheral wall of the housing. The peripheral wall of the housing may further comprise four side walls having a first length and the sleeve has a second length, wherein the first length is longer than the second length. The peripheral wall of the housing may further comprise a front wall and a rear wall having a first height, and the sleeve has a second height, wherein the first height is longer than the second height. The peripheral wall of the housing further comprises a front wall and rear wall having a first width and the sleeve has a second width, wherein the first width is longer than the second width. The peripheral wall of the housing may further comprise at least three side walls and the sleeve is mounted in the housing to form at least three gaps between the sleeve and at least three side walls. The oven may further comprise a sleeve mounted in the housing to form a rear gap between the sleeve and a rear wall. The sleeve may further comprise a top surface, a bottom surface, and two side surfaces. The sleeve may be in the shape of a tube, such as a rectangular tube. The sleeve may comprise a first end positioned adjacent to a first end wall and a second end positioned adjacent to a second end wall. The sleeve may have a first opening adjacent to one end wall and a second opening adjacent to the other end wall. The oven may further comprise a heating element positioned adjacent an end wall and adjacent to the sleeve.

The sleeve may surround the heating element. The housing may further comprise at least three side walls, wherein at least three gaps are positioned between the sleeve and the at least three side walls. The oven may further comprise a fan positioned adjacent to one end wall, wherein the sleeve is in coaxial alignment with the fan. One end wall may further comprise a central door. The oven may further comprise a fan having a blade and a central axis perpendicular to the blade, the blade having a first length equal to the radius of the fan. Optionally, the sleeve is in the shape of a tube having a radius which is longer than the radius of the fan. The oven may comprise at least one gap which traverses the apparatus from end wall to end wall. The first and second gaps may have a width of between about 0.5 cm to 20 cm, preferably about 2 cm. The second gap may have a width of between about 0.5 cm and about 20 cm and traverses the apparatus from end wall to end wall, preferably about 2 cm. The oven may further comprise a fan that has an adjustable rate of rotation. The oven may be disposed within a gas chromatography system comprising a carrier gas delivery device; an injector system; and a detector system.

The objectives of the present invention are met by providing a gas chromatography oven comprising: a housing having a front wall, a rear wall, and four side walls; and a sleeve comprising a top surface, a bottom surface and two side surfaces mounted within the housing, wherein the four side walls have a first length longer than the length of the top surface, bottom surface and two side surfaces such that at least three gaps are formed between the sleeve and the housing. The four side walls may have a first width longer than the width of the top surface, bottom surface and two side surfaces such that at least three gaps are formed between the sleeve and the housing. The at least three gaps are located between the sleeve and the side walls. At least one gap is located between the sleeve and the front wall. Optionally, at least one gap is located between the sleeve and the rear wall. Optionally the oven comprises four gaps located between the sleeve and the four side walls. The oven further comprises a housing having a longitudinal axis between the four side walls, and the sleeve has a longitudinal axis between the top surface, bottom surface and two side surfaces, wherein the longitudinal axis of the housing is in coaxial alignment with the longitudinal axis of the sleeve. The rear wall is separable from the housing. Optionally, the rear wall further comprises a door. A fan may be disposed inside the housing adjacent to the rear wall. Optionally, the fan is connected to a variable speed motor. Furthermore, the oven may further comprise a heating element adjacent to the fan. The oven may further comprise a baffle adjacent to the heating element. The oven may further comprise gaps connected to a plenum positioned adjacent to the rear wall. The oven may be further disposed within an external housing, wherein the external housing connects at least one carrier gas supply; at least one sample injection system; and at least one detector system. The external housing may further comprise a raised bottom surface and an exhaust chute adjacent to the bottom surface.

The objectives of the present invention are further met by providing a gas chromatography system comprising a gas chromatography oven having a housing having two end walls and a peripheral wall, a sleeve disposed within the housing, the sleeve having a peripheral wall spaced apart from the peripheral wall of the housing; and a fluid path defined by an interior of the sleeve, a first gap between at least one end wall and the sleeve, and a second gap between the sleeve and the peripheral wall of the housing, wherein air is forced through the sleeve, through the first gap between at least one end wall and the sleeve, and through the second gap between the sleeve and the peripheral wall of the housing; and at least one additional component selected from the group consisting of carrier gas supply, pressure regulator, flow controller, rotometer, gas flow line, injector system, autosampler, injector, column, detector, soap-bubble meter, electrometer, ADC, data system and combinations thereof. The system may further comprise a detector selected from the group consisting of flame ionization detector, thermal conductivity detector, electron capture detector, environmental specific detector, photoionization detector, nitrogen phosphorous detector, and combinations thereof. The system may further comprise a raised external housing comprising an exhaust chute adjacent to the bottom of the external housing. The system may further comprise an oven comprising a fan, a baffle, and a heater in coaxial alignment with the sleeve.

The objectives of the present invention are further met by providing a method of cooling a gas chromatography oven comprising: blowing air through a fluid path defined by an interior of a sleeve, a first gap between at least one end wall and the sleeve, and a second gap between the sleeve and a peripheral wall of a housing, wherein air is forced through the sleeve, through the first gap between at least one end wall and the sleeve, and through the second gap between the sleeve and the peripheral wall of the housing. The method may further include: directing the air towards a second gap. The step of blowing air may further comprise the step of changing air speed by adjusting a motor.

BRIEF DESCRIPTION OF THE ILLUSTRATED EMBODIMENTS

DETAILED DESCRIPTION OF THE DRAWINGS

Figure 1:
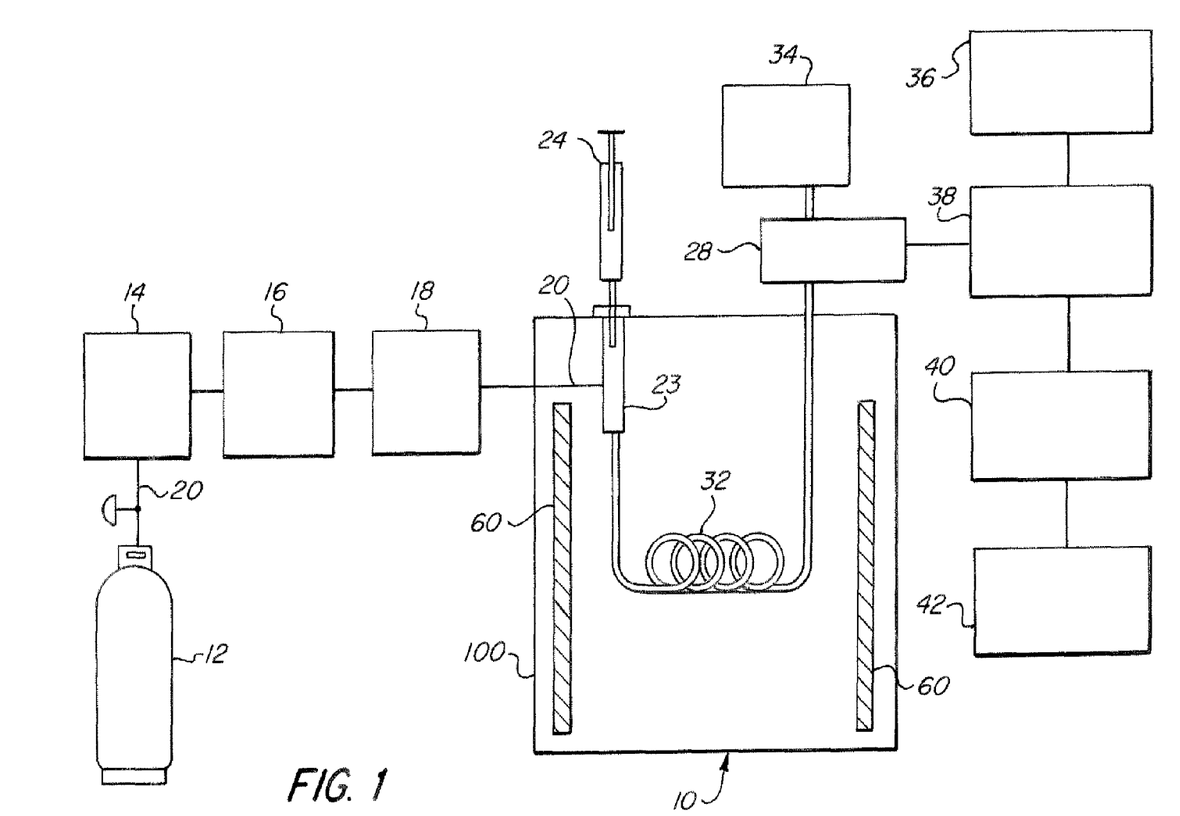
FIG. 1 is a schematic view of a gas chromatography system of the present invention.

Referring now to FIG. 1, a schematic view of a gas chromatography system 10 of the present invention is shown. Carrier gas supply 12 is shown connected to oven 100. Carrier gases typically include noble gases such as helium, neon, or argon, however any suitable gas may be used. Various control devices such as pressure regulator 14, flow controller 16, and rotometer 18 regulate and measure the rate of fluid flow between supply 12 and oven 100. Gas flow line 20 enters the oven and is connected to injector system 24. Injector system 24 is provided to load a sample with analyte(s) of interest into oven 100, which may include an autosampler. Gas from first gas flow line 20 and sample with analyte of interest combine in injector 23 and pass into column 32 located in oven 100 and connected to detector 28. A wide range of suitable detectors 28 for sensitivity and selectivity may be used with the present invention, including but not limited to a flame ionization detector, thermal conductivity detector, electron capture detector, environmental specific detector, photoionization detector, nitrogen phosphorous detector, and combinations thereof. Gas chromatography system 10 may further include soap-bubble meter 34 for measuring the flow of gas at ambient temperature and pressure over a wide range of flow rates. Recorder 36 is shown connected to electrometer or bridge 38, which is connected to ADC 40 and data system 42, all for converting a signal into qualitative information about an analyte of interest. Sleeve 60 is added to improve heat exchange during the cooling cycle.

Figure 2:
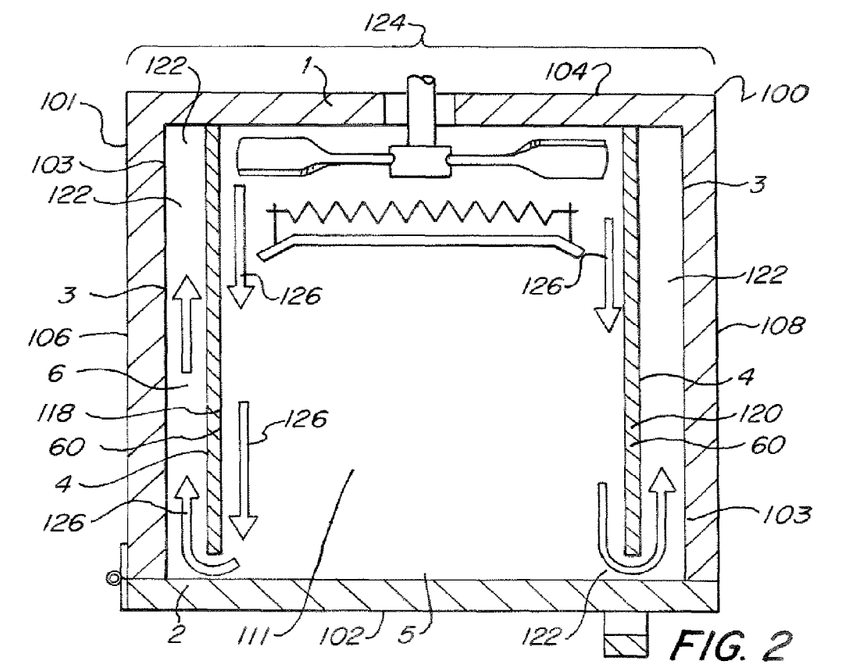
FIG. 2 is a schematic top view of a gas chromatography oven of the present invention.

Referring now to FIG. 2, a schematic top view of gas chromatography (GC) oven 100 is shown comprising a housing 101 having two end walls 1 & 2 and peripheral wall 3. Sleeve 60 is disposed within housing 101, sleeve 60 having a peripheral wall 4 spaced apart from the peripheral wall 3 of housing 101. As used herein the term sleeve means a passageway that allows air to pass through, no particular shape or size is necessary. A fluid path defined by an interior of the sleeve 111, a first gap 5 between at least one end wall 2 and sleeve 60, and a second gap 6 between sleeve 60 and the peripheral wall 3 of housing 101 is shown. In the illustrated embodiments, air is moved in the direction of arrows 126 through sleeve 60, through the first gap 5 between at least one end wall 2 and sleeve 60, and into the second gap 6 between sleeve 60 and peripheral wall 3 of housing 101.

Figure 3:
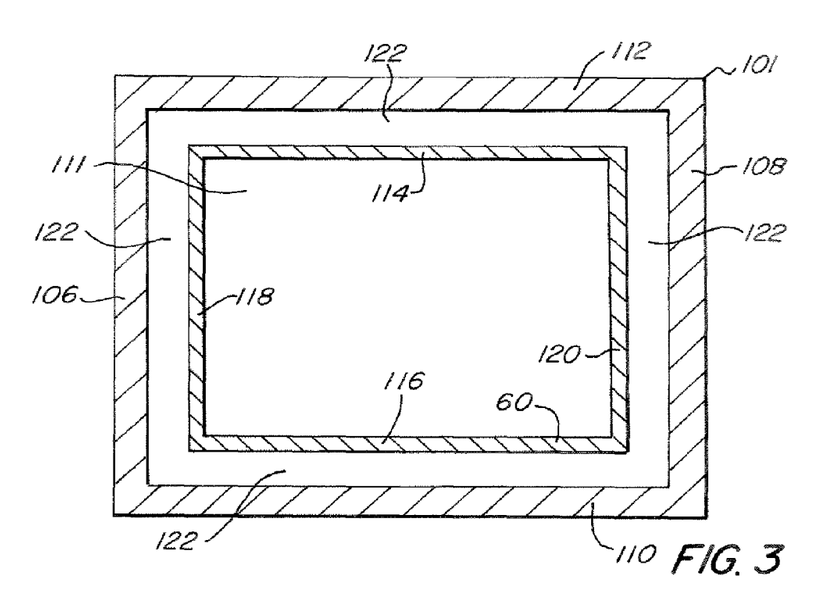
FIG. 3 is a front plan view of the gas chromatography oven of FIG. 2.

With reference to FIG. 2 and FIG. 3, housing 101 is shown having a front wall 102, a rear wall 104, and two side walls 106, 108. Housing 101 comprises two additional walls 110 and 112 (not shown in FIG. 2). Sleeve 60 has a top surface 114 (not shown in FIG. 2), a bottom surface 116 (not shown in FIG. 2) and two side surfaces 118 and 120 mounted within housing 100. The four side walls 106, 108, 110, and 112 have a first length 120 longer than the length of the top surface 114 (not shown in FIG. 2), bottom surface 110 (not shown in FIG. 2) and two side surfaces 118 and 120 such that at least three gaps 122 are formed between sleeve 60 and housing 101.

With continued reference to FIGS. 2 and 3, gaps 122 may be positioned above, below, in front of, behind, and along the sides of sleeve 60 between housing 101. Sleeve 60 is mounted within housing 101 by ways in which one of ordinary skill in the art would mount a sleeve, including soldering and bolting techniques. The four side walls of housing 101 have a first width 124 longer than the width of the top surface, bottom surface and two side surfaces of sleeve 60 such that at least three gaps 122 are formed between sleeve 60 and housing 101. Three or more gaps 122 may be located between sleeve 60 and side walls 106, 108, 110, 112. At least one gap 122 may also be located between sleeve 60 and front wall 102. At least one gap 122 may also be located between sleeve 60 and the rear wall 104. Moreover, oven 100 may be configured to have four gaps 122 located between sleeve 60 and the four side walls 102, 104, 106, 108.

Still referring to FIG. 2, gap 122 is shown between sleeve 60 and housing 101. Gap 122 is of predetermined shape and size. Here, gap 122 is shown traversing the interior length, width, and height of housing 101. The width between housing 101 and sleeve 60 can be between about 0.5 cm to 30 cm, but in some embodiments may be about 2 cm and 10 cm, and in further embodiments about 4 cm. During ventilation, ambient air enters through a sliding door (not shown in FIG. 2) built into wall 104, then travels through the interior portion 111 of sleeve 60 in the direction of arrow 126. Upon collision with front wall 102, the cooling air moves up, down, and laterally into gaps 122 between housing 101 and sleeve 60. The cooling air then travels back through oven 100 over oven skin 103 into a plenum (not shown in FIG. 2) resulting in a thermal cool down.

Referring now to FIG. 3, a front plan view of the gas chromatography oven of FIG. 2 is shown. Housing 101, made to predetermined dimensions, is shown having at least four side walls 106, 108, 110, and 112. Sleeve, also of predetermined dimensions, has a top surface 114, a bottom surface 116 and two side surfaces 118 and 120 mounted within housing 101. The four side walls 106, 108, 110, and 112 have longer and wider dimensions than the length of the top surface 114, bottom surface 116, and two side surfaces 118 and 120 such that at least three gaps 122 are formed between sleeve 60 and housing 101.

Figures 4, 5:
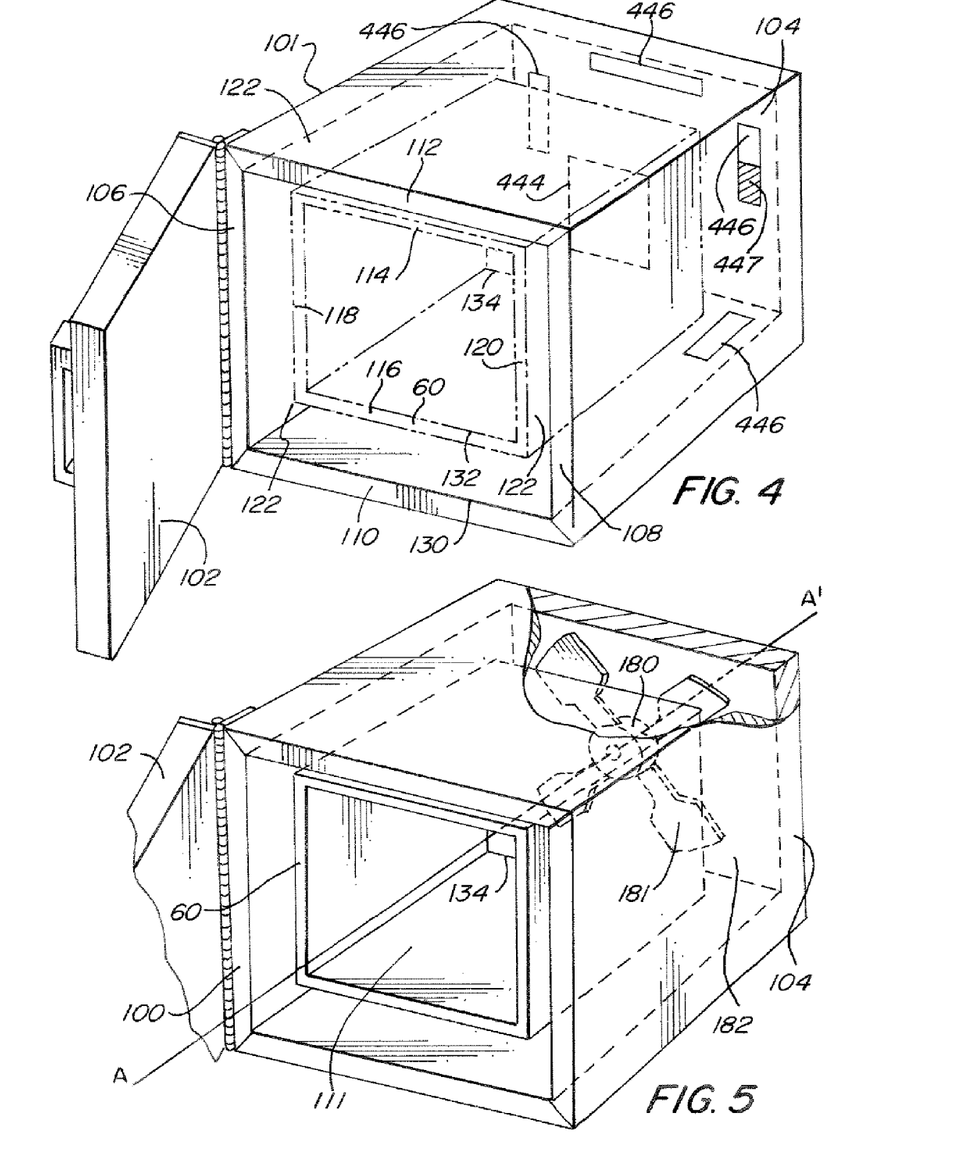
FIG. 4 is an isometric view of the gas chromatography oven of FIG. 2 with the sleeve shown partially in phantom.
FIG. 5 is a front view of a gas chromatography oven of FIG. 2 with components in coaxial alignment.

Referring now to FIG. 4 there is shown an isometric view of the gas chromatography oven of FIG. 2 with the sleeve 60 shown partially in phantom. Housing 101, made to predetermined dimensions, is shown having at least four side walls 106, 108, 110, and 112. Sleeve 60, also of predetermined dimensions, has a top surface 114, a bottom surface 116 and two side surfaces 118 and 120 mounted within housing 101. The four side walls 106, 108, 110, and 112 have longer, wider and higher dimensions than the length of the top surface 114, bottom surface 116, and two side surfaces 118 and 120 such that at least three gaps 122 are formed between sleeve 60 and housing 101. Oven 100 is shown having a first opening 130. Front wall 102 of housing 101 acts as an access door to oven 100 opening and closing first opening 130, and may be attached to housing 101 by one or more hinges. Sleeve 60 is also shown having a front or first opening 132 adjacent to the first opening 130. Also sleeve 60 comprises a second opening 134 adjacent to rear wall 104. Fluid entry or door 444 is shown in rear wall 104 which is opened during the ventilation process to provide cooling air to oven 100. Optionally fluid entry 444 may be in coaxial alignment with fan shaft (not shown in FIG. 4).

With continued reference to FIG. 4 at least one fluid exit 446 is shown in housing 101. Fluid exit 446 is of predetermined shape and size and positioned in fluid communication with gap 122. Fluid exit 446 can be positioned within at least a portion of at least one wall of housing 101 to facilitate exit of the cooling fluid from at least one fluid gap 122, where the at least one fluid exit 446 is in fluid communications with the fluid gap 122. Optionally, second, third and fourth fluid exits 446 may be positioned in housing 101. Fluid exit 446 may comprise a door 447 capable of adjusting fluid flow passing through the fluid exit. Door 447 may be configured as a controllable sliding door suitable for opening and closing fluid exit 446.

Referring now to FIG. 5 a front view of a gas chromatography oven of FIG. 2 with components in coaxial alignment along axis A-A' is shown. Sleeve 60 is disposed within oven 100. Fan 180 is shown located within oven cavity 182 between rear wall 104 and second opening 134 of sleeve 60. Fan 180 may be a conventional fan used in gas chromatography ovens and have one or more fan blades 181 for directed air through oven 100 and sleeve 60. Fan 180 rotates about a fan axis (not shown in FIG. 5). When the ventilation system is open, fan 180 directs ambient air into inner portion 111 of sleeve 60. The predominant flow directs air towards front wall 102 which, when closed, redirects the air as described herein. In some embodiments, the fan axis extends through intake and exhaust apertures (not shown in FIG. 5) in coaxial alignment with the aperture centers. In alternative embodiments, the fan axis extends through intake and exhaust apertures without being aligned with the aperture centers.

Figure 6:
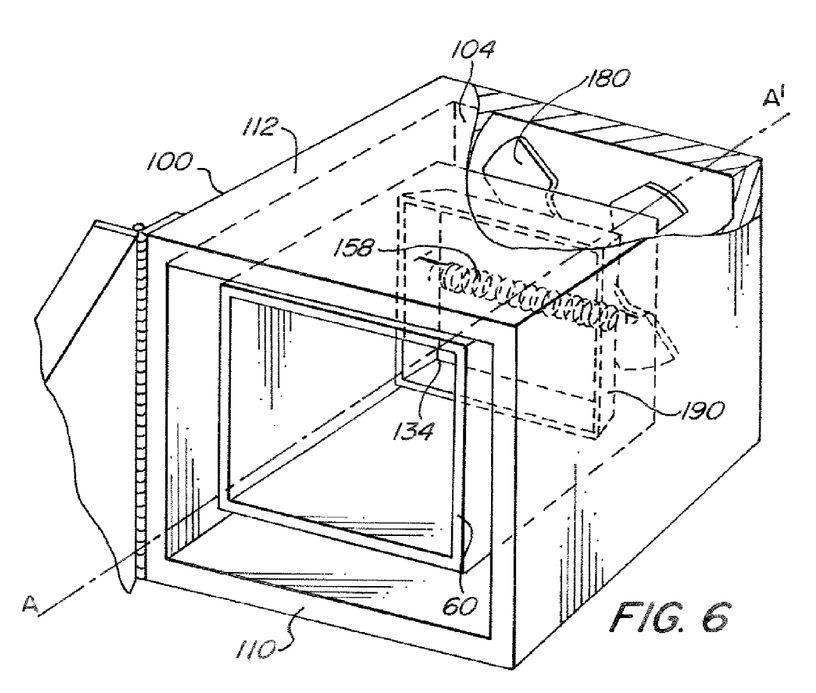
FIG. 6 is a front view of a gas chromatography oven of FIG. 2 with components in coaxial alignment.

Referring now to FIG. 6 a front view of a gas chromatography oven of FIG. 2 with components in coaxial alignment along axis A-A' is shown. Sleeve 60 is disposed within oven 100. Fan 180 is shown located within oven cavity 182 between rear wall 104 and second opening 134 of sleeve 60. Heating element 158 is mounted inside oven 100 in close proximity to rear wall 104 and fan 180. Heater 158 may be any heater suitable for use in a gas chromatography oven, such as an electric coil heater. Heater 158 is supplied with sufficient current to enable the temperature of the air in oven 100 to heat up to about 500° C. In some embodiments, heater 158 includes a resistive heater and an amplifier. To either end of heater 158 shields may be added to protect column (not shown in FIG. 6) from direct radiant heat. Baffle 190 is also shown, which may include an integral protective screen in the center portion. Baffle 190 may be made of stainless steel and attached to housing 101 between top side wall 112 and bottom side wall 110 by fasteners known in the art. Heater 158 is positioned between fan 180 and baffle 190. Baffle 190 is used to constrain the flow from the fan and enhance the pressure gradient across oven 100. In embodiments, the internal elements, including sleeve 60, fan 180, heater 158, and baffle 190 are in coaxial alignment within housing 101 along axis A-A'.

Figure 7:
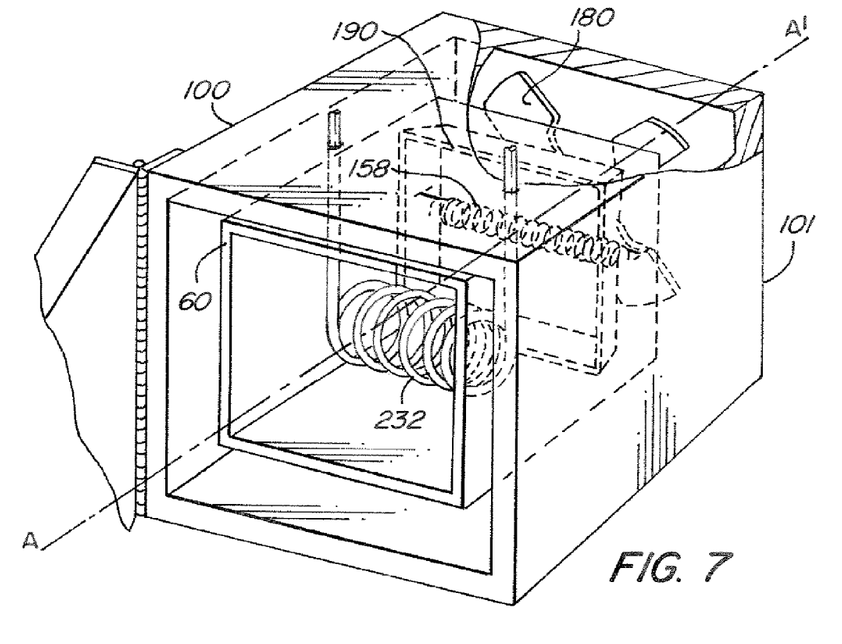
FIG. 7 is a front view of a gas chromatography oven of FIG. 2 with components in coaxial alignment.

Referring now to FIG. 7, a front view of a gas chromatography oven of FIG. 6 with components in alignment is shown. The internal elements common to each of the embodiments of gas chromatography oven are shown including sleeve 60, fan 180, heater 158, and baffle 190 substantially aligned within housing 101 along axis A-A'. Column 232 is positioned in the interior of oven 100 adjacent to baffle 190. Column 232 may be held in place by brackets (not shown in FIG. 7) or other means known in the art.

Figure 8:
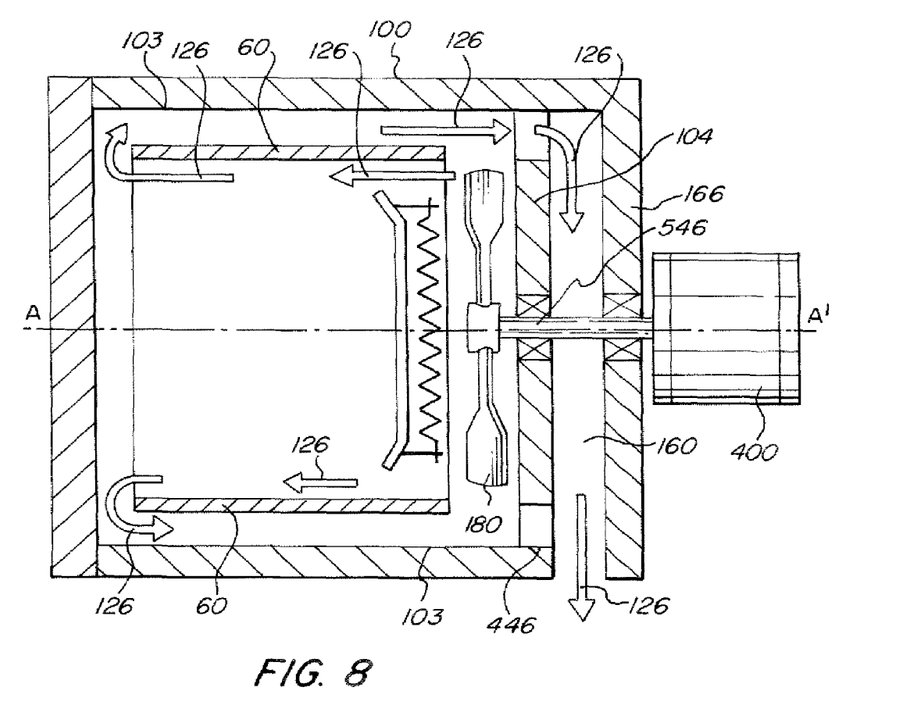
FIG. 8 is a partial cross-sectional side view taken along line A-A' of FIG. 7 with plenum.

FIG. 8 is a partial cross-sectional view taken along line A-A' of FIG. 7. The only basic difference between the embodiment shown in FIGS. 6 & 7 is the use of plenum chamber 160 to vent air through the back portion and bottom of housing 101. Plenum chamber 160 as shown in FIG. 8 has a depth from plenum wall 166 to rear wall 104. During ventilation, air travels in the direction of arrow 126. Ambient air passes through sleeve 60, then passes over oven skin 103 of oven 100 while returning to plenum chamber 160 prior to exiting the apparatus. Fan motor 400 may be a brush motor or a brushless motor, and in embodiments, a variable speed brushless motor capable of spinning fan 180 between about 1000 RPM to about 4500 RPM and above. Shown below in FIG. 9 is a more preferred embodiment where plenum chamber 160 is configured adjacent to fan 180 within housing 101.

Figure 9:
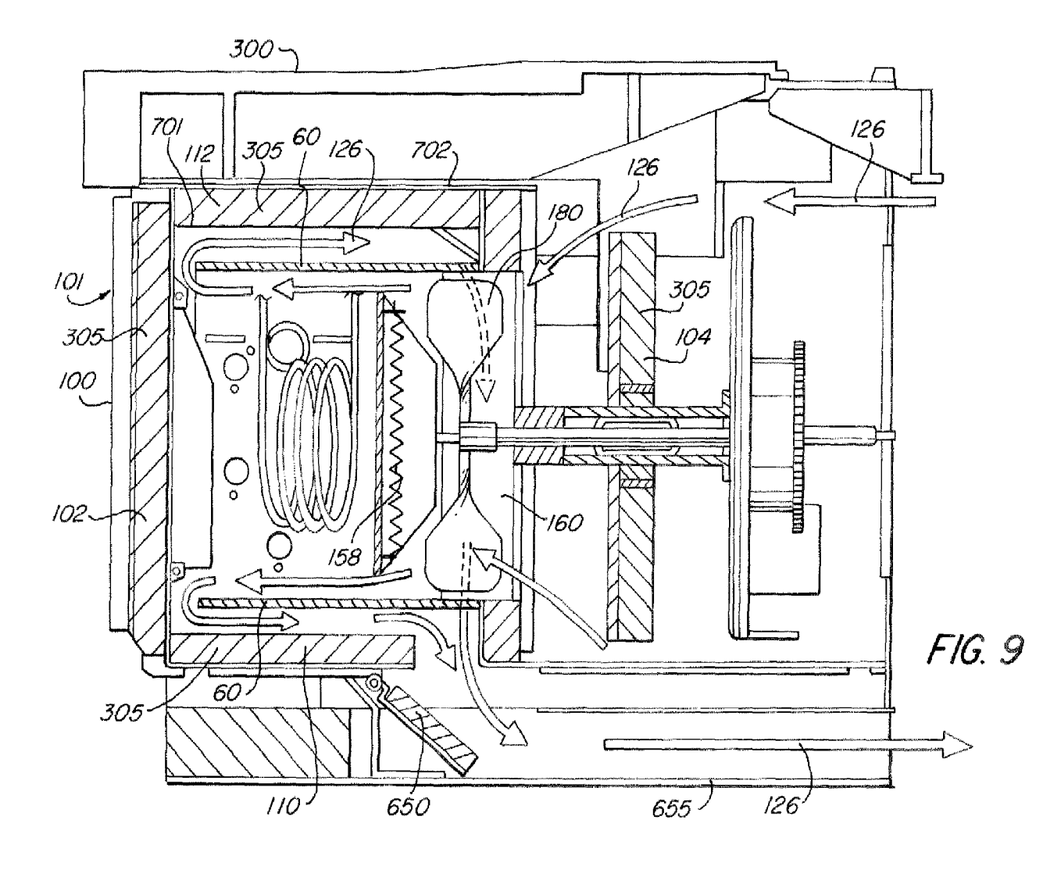
FIG. 9 is a schematic view of gas chromatography system with oven of FIG. 2.

FIG. 9 is a schematic view of gas chromatography system with oven of FIG. 2. Gas chromatography oven 100 is shown positioned within gas chromatography exterior housing unit 300. Exterior housing 300 may be configured to accommodate some or all of the various components shown in FIG. 1 above. Oven 100 can be made of materials which enhance dynamic performance. Oven walls have a thickness ranging from about 1 cm to about 8 cm, and in some embodiments, about 2 cm to about 2.5 cm between the inner edge 701 of insulator 305 and outer face 702. The outer face 702 or skin consists of a metal, e.g. aluminum or steel, or a high temperature plastic, typically having a thickness of about 2 mm. Positioned adjacent to outer face 702 is insulator 305 made of thermal ceramic material such as microporous insulation designed for use in high temperature applications. Insulator 305 is between about 0.5 cm to about 20 cm thick, and in some embodiments, about 3.5 cm. In some embodiments insulator 305 is made of BTU-Block Board 1807/18 ceramic material having a relatively low thermal conductivity and heat loss. It has been found that this brand of thermal ceramic material promotes a highly efficient cool down due to its relatively low thermal mass and heat storage capacity. Although other thermal ceramic products are suitable for use in the present invention, such as a ceramic fiber known as Kaowool blanket, other ceramic fibers may be less preferred. In some embodiments, insulator 305 is disposed throughout housing 101 inside front wall 102, rear wall 104, side walls 106, 108, 110 and 112. Interior edge 701 of insulator 305 can make up the interior edge of front wall 102, rear wall 104, side walls 106, 108, 110 and 112.

Still referring to FIG. 9, rear wall 104 is a sliding member capable of sliding away from the remaining portions of oven 100. During ventilation, rear wall 104 is extended away from oven 100 and its components. The extended position allows air to travel through external housing 300 into oven 100 and sleeve 60. Optionally, one or more doors may be positioned in rear wall 104 for ventilation.

After a run, a cooling cycle occurs where heating element 158 is turned off and rear wall 104 is opened. Ambient air is pulled by fan 180 from outside oven 100 through exterior housing unit 300 in the direction of arrows 126. Air circulates past open rear wall 104, through the apparatus and into sleeve 60. The airflow is extremely direct and not hindered by counter airflow. The heat transfer is compounded by the dual action of cooler air contacting the outside of sleeve 60, as well as insulator 305. In some embodiments, the airflow is directed out the back of the oven into a plenum portion 160 configured adjacent to fan 180. In some embodiments, trap door 650 is open during the cool down cycle such that cooling air is capable of venting through exhaust shoot 655 located in the lowest portion of exterior housing unit 300. Accordingly, in comparison to conventional units, exterior housing unit 300 is raised to accommodate exhaust shoot 655.

Figure 10:
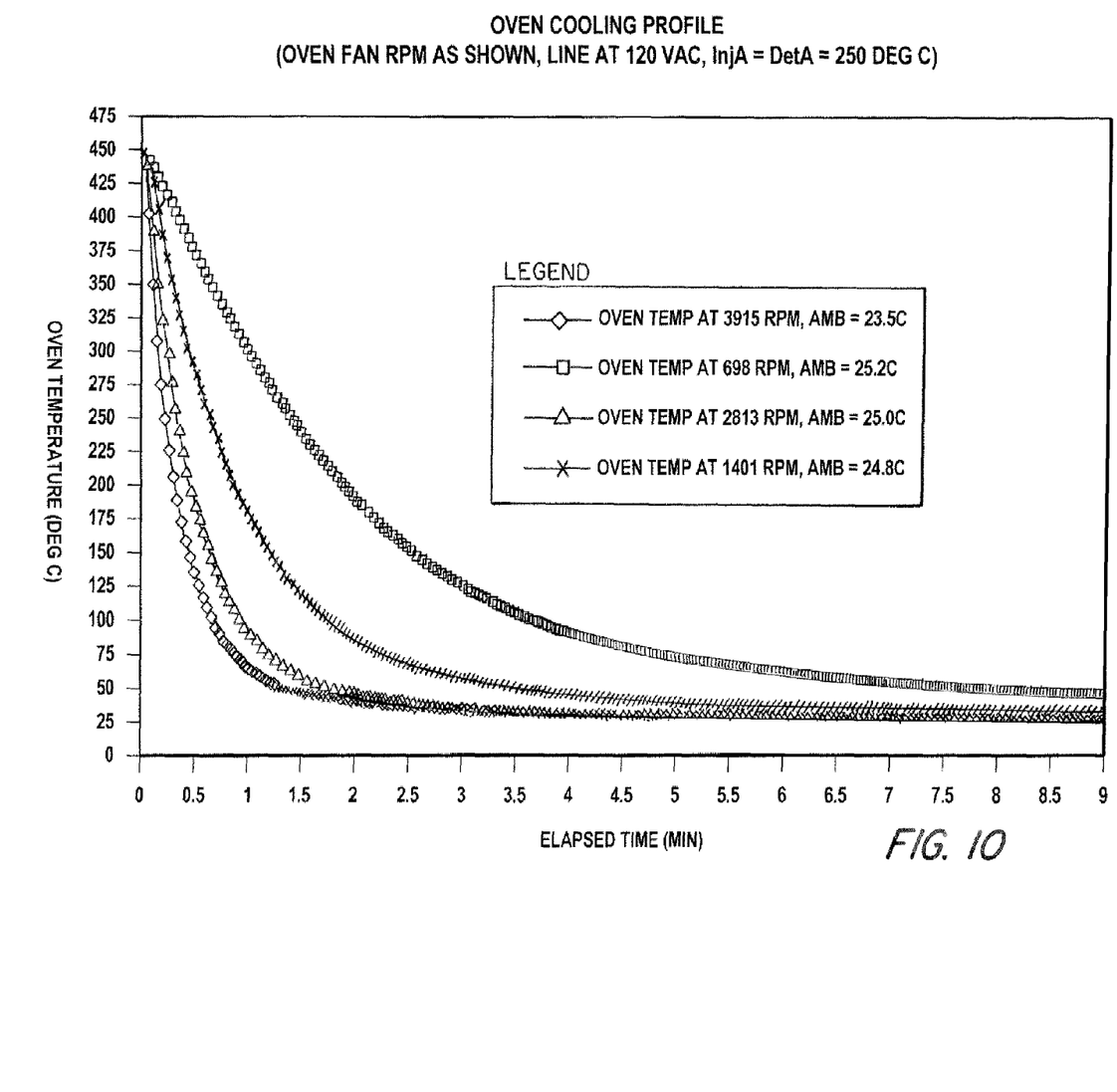
FIG. 10 is a cooling profile graph of oven temperature over time using system of FIG. 9.

FIG. 10 is a graph of an oven cooling profile using an embodiment of the present invention. Four cool down profiles are shown for four different fan rates including 3915 RPM, 698 RPM, 2813 RPM, and 1401 RPM. Rapid heat exchange between the oven and surrounding environment using different fan speeds was observed.

Without departing from the spirit and scope of this invention, one of ordinary skill in the art can make various changes and modifications to the invention to adapt it to various usages and conditions. As such, these changes and modifications are properly, equitably, and intended to be, within the full range of equivalents of the following claims.

What is claimed is:

1. A gas chromatography oven comprising:
a housing having two end walls and a peripheral wall,
a sleeve disposed within the housing, said sleeve having a peripheral wall spaced apart from the peripheral wall of the housing;
a fluid path defined by an interior of said sleeve, a first gap between at least one of said two end walls and said sleeve, and a second gap between the peripheral wall of said sleeve and the peripheral wall of said housing, wherein air is forced through said sleeve, through the first gap between at least one end wall and said sleeve, and into the second gap between the peripheral wall of said sleeve and the peripheral wall of said housing;
a heating element positioned adjacent an end wall and adjacent to the sleeve; and
wherein the sleeve surrounds the heating element.

2. The oven of claim 1 wherein the peripheral wall of said housing further comprises four side walls having a first length and said sleeve has a second length, wherein the first length is longer than the second length.

3. The oven of claim 1 wherein the peripheral wall of said housing further comprises a front wall and a rear wall having a first height, and said sleeve has a second height, wherein the first height is longer than the second height.

4. The oven of claim 1 wherein the peripheral wall of said housing further comprises a front wall and rear wall having a first width and said sleeve has a second width, wherein said first width is longer than said second width.

5. The oven of claim 1 wherein said peripheral wall of said housing further comprises at least three side walls and said sleeve is mounted in the housing to form at least three gaps between said sleeve and at least three side walls.

6. The oven of claim 1 wherein the sleeve is mounted in the housing to form a rear gap between said sleeve and a rear wall.

7. The oven of claim 1 wherein the sleeve further comprises a top surface, a bottom surface, and two side surfaces.

8. The oven of claim 1 wherein the sleeve is in the shape of a tube.

9. The oven of claim 1 wherein the sleeve is in the shape of a rectangular tube.

10. The oven of claim 1 wherein the sleeve comprises a first end positioned adjacent to a first end wall and a second end positioned adjacent to a second end wall.

11. The oven of claim 10 wherein the sleeve has a first opening adjacent to one end wall and a second opening adjacent to the other end wall.

12. The oven according to claim 1 further comprising a fan positioned adjacent to one end wall, wherein the sleeve is in coaxial alignment with the fan.

13. A gas chromatography oven comprising:
a housing having two end walls and a peripheral wall,
a sleeve disposed within the housing, said sleeve having a peripheral wall spaced apart from the peripheral wall of the housing; and
a fluid path defined by an interior of said sleeve, a first gap between at least one of said two end walls and said sleeve, and a second gap between the peripheral wall of said sleeve and the peripheral wall of said housing, wherein air is forced through said sleeve, through the first gap between at least one end wall and said sleeve, and into the second gap between the peripheral wall of said sleeve and the peripheral wall of said housing; and
wherein one end wall comprises a central door.

14. The oven according to claim 13, further comprising a fan having a blade and a central axis perpendicular to the blade, the blade having a first length equal to the radius of the fan.

15. The oven according to claim 14 wherein the sleeve is in the shape of a tube having a radius which is longer than the radius of the fan.

16. The oven according to claim 13 wherein at least one gap traverses the apparatus from end wall to end wall.

17. The oven according to claim 13 wherein the first and second gaps have a width of between about 0.5 cm to 20 cm.

18. The oven according to claim 13 wherein the second gap has a width of between about 0.5 cm and about 20 cm and traverses the apparatus from end wall to end wall.

19. The oven according to claim 13 further comprising a fan that has an adjustable rate of rotation.

20. The oven according to claim 13 disposed within a gas chromatography system comprising a carrier gas delivery device; an injector system; and a detector system.

21. The oven of claim 13 wherein the four side walls have a first width longer than the width of the top surface, bottom surface and two side surfaces such that at least three gaps are formed between said sleeve and said housing.

22. The oven of claim 13 wherein the at least three gaps are located between said sleeve and said side walls.

23. The oven of claim 13 wherein at least one gap is located between said sleeve and the front wall.

24. The oven of claim 13 wherein at least one gap is located between said sleeve and the rear wall.

25. The oven of claim 13 wherein four gaps are located between said sleeve and the four side walls.

26. The oven of claim 13 wherein said housing has a longitudinal axis between the four side walls, and said sleeve has a longitudinal axis between the top surface, bottom surface and two side surfaces, wherein the longitudinal axis of said housing is in coaxial alignment with the longitudinal axis of said sleeve.

27. A gas chromatography oven comprising:
a housing having a front wall, a rear wall, and four side walls;
a sleeve comprising a top surface, a bottom surface and two side surfaces mounted within the housing, wherein the four side walls have a first length longer than the length of the top surface, bottom surface and two side surfaces such that at least three gaps are formed between said sleeve and said housing; and
wherein the rear wall further comprises a door.

28. A gas chromatography oven comprising:
a housing having a front wall, a rear wall, and four side walls;
a sleeve comprising a top surface, a bottom surface and two side surfaces mounted within the housing, wherein the four side walls have a first length longer than the length of the top surface, bottom surface and two side surfaces such that at least three gaps are formed between said sleeve and said housing; and
wherein the rear wall is separable from the housing.

29. The oven of claim 28 further wherein a fan is disposed inside said housing adjacent to the rear wall.

30. The oven of claim 29 wherein said fan is connected to a variable speed motor.

31. The oven of clam 29 further comprising a heating element adjacent to said fan.

32. The oven according to claim 28 wherein the gaps are connected to a plenum positioned adjacent to the rear wall.

33. A gas chromatography oven comprising:
a housing having a front wall, a rear wall, a top wall, a bottom wall, a left side wall, and a right side wall;
a sleeve comprising a top surface, a bottom surface, a left surface, and a right surface mounted within the housing, wherein said top, bottom, left side, and right side walls each have a first length longer than the length of the top surface, bottom surface and two side surfaces such that there is a first gap between said top surface and said top wall, a second gap between said bottom surface and said bottom wall, a third gap between said left surface and said left side wall, and a fourth gap between said right surface and said right side wall;
a fan is disposed inside said housing adjacent to the rear wall; and
a heating element adjacent to said fan; and
a baffle adjacent to said heating element.

34. A gas chromatography oven comprising:
a housing having a front wall, a rear wall, and four side walls;
a sleeve comprising a top surface, a bottom surface and two side surfaces mounted within the housing, wherein the four side walls have a first length longer than the length of the top surface, bottom surface and two side surfaces such that at least three gaps are formed between said sleeve and said housing; and wherein the external housing connects at least one carrier gas supply; at least one sample injection system; and at least one detector system.

35. The apparatus of claim 34 wherein the external housing further comprises a raised bottom surface and an exhaust chute adjacent to the bottom surface.

36. A gas chromatography oven according to claim 34, where the housing includes at least one fluid exit, and the fluid gap is in fluid communications with the at least one fluid exit.

37. A gas chromatography oven according to claim 34, where the sleeve comprises a heating element.

38. A gas chromatograph oven according to claim 34, further comprising a fan positioned to drive at least one fluid from the fluid entry into the sleeve.

39. A gas chromatography oven, comprising:
a housing having a fluid entry;
a sleeve positioned within the housing to provide a fluid gap between the inner surface of the housing and the outer surface of the sleeve, where the sleeve is coupled to the fluid entry;
where fluid from the fluid entry traverses the inner layer of the sleeve and thereafter the outer layer of the sleeve via the fluid gap; and
where the fluid entry and the sleeve are concentric.

40. A gas chromatography oven, comprising:
a housing having a fluid entry;
a sleeve positioned within the housing to provide a fluid gap between the inner surface of the housing and the outer surface of the sleeve, where the sleeve is coupled to the fluid entry;
where fluid from the fluid entry traverses the inner layer of the sleeve and thereafter the outer layer of the sleeve via the fluid gap; and
where the housing includes a wall at least a portion of which is adjustable to prevent fluid from entering the fluid entry.

41. A gas chromatography oven, comprising:
a housing having a fluid entry;
a sleeve positioned within the housing to provide a fluid gap between the inner surface of the housing and the outer surface of the sleeve, where the sleeve is coupled to the fluid entry;
where fluid from the fluid entry traverses the inner layer of the sleeve and there-after the outer layer of the sleeve via the fluid gap; and
at least one fluid exit ;and
a wall at least a portion of which is adjustable to prevent fluid from exiting the at least one fluid exit.

42. A method of cooling a gas chromatography oven, the method comprising:
providing a housing having a fluid entry;
positioning a sleeve within the housing to provide a fluid gap between the inner surface of the housing and the outer surface of the sleeve, where the sleeve is coupled to the fluid entry, and where fluid from the fluid entry traverses the inner layer of the sleeve and thereafter the outer layer of the sleeve via the fluid gap;

providing a cooling fluid to the fluid entry; and where positioning includes concentrically positioning the sleeve and the fluid entry.

43. A method according to claim 42, where the housing includes at least one fluid exit, and the fluid gap is in fluid communications with at least one fluid exit.

44. A method according to claim 42, further comprising controlling a fan positioned at the fluid entry to drive the cooling fluid.

45. A method of cooling a gas chromatography oven, the method comprising:

providing a housing having a fluid entry;

positioning a sleeve within the housing to provide a fluid gap between the inner surface of the housing and the outer surface of the sleeve, where the sleeve is coupled to the fluid entry, and where fluid from the fluid entry traverses the inner layer of the sleeve and thereafter the outer layer of the sleeve via the fluid gap;

providing a cooling fluid to the fluid entry; and adjusting at least a portion of at least one wall of the housing to facilitate entry of the cooling fluid to the fluid entry.

46. A method of cooling a gas chromatography oven, the method comprising:

providing a housing having a fluid entry;

positioning a sleeve within the housing to provide a fluid gap between the inner surface of the housing and the outer surface of the sleeve, where the sleeve is coupled to the fluid entry, and where fluid from the fluid entry traverses the inner layer of the sleeve and thereafter the outer layer of the sleeve via the fluid gap;

providing a cooling fluid to the fluid entry; and adjusting at least a portion of at least one wall of the housing to facilitate exit of the cooling fluid from at least one fluid exit, where the at least one fluid exit is in fluid communications with the fluid gap.

* * * * *